US012661439B2

(12) United States Patent
Prime et al.

(10) Patent No.: US 12,661,439 B2
(45) Date of Patent: Jun. 23, 2026

(54) METHOD FOR REGULATING THE OPERATION OF A MILK PUMP

(71) Applicant: MEDELA AG, Baar (CH)

(72) Inventors: Danielle Prime, Lucerne (CH); Leon Mitoulas, Stirling Wa (AU)

(73) Assignee: MEDELA AG, Baar (CH)

( * ) Notice: Subject to any disclaimer, the term of this patent is extended or adjusted under 35 U.S.C. 154(b) by 962 days.

(21) Appl. No.: 17/798,831

(22) PCT Filed: Feb. 15, 2021

(86) PCT No.: PCT/EP2021/053592
§ 371 (c)(1),
(2) Date: Aug. 10, 2022

(87) PCT Pub. No.: WO2021/160875
PCT Pub. Date: Aug. 19, 2021

(65) Prior Publication Data
US 2023/0083998 A1     Mar. 16, 2023

(30) Foreign Application Priority Data

Feb. 14, 2020     (EP) ..................................... 20157295

(51) Int. Cl.
*A61M 1/06*          (2006.01)
(52) U.S. Cl.
CPC ... *A61M 1/0693* (2021.05); *A61M 2205/3334* (2013.01); *A61M 2205/52* (2013.01)
(58) Field of Classification Search
CPC ............................................ A61M 1/06–0697
See application file for complete search history.

(56) References Cited

U.S. PATENT DOCUMENTS

| | | | |
|---|---|---|---|
| 4,964,851 A | 10/1990 | Larsson |
| 5,007,899 A | 4/1991 | Larsson |
| (Continued) | | | |

FOREIGN PATENT DOCUMENTS

| | | |
|---|---|---|
| CN | 1683022 A | 10/2005 |
| DE | 202008016450 U1 | 3/2009 |
| (Continued) | | |

OTHER PUBLICATIONS

International Search Report for International Application No. PCT/EP2021/053592, dated Apr. 30, 2021.

(Continued)

*Primary Examiner* — Courtney B Fredrickson
(74) *Attorney, Agent, or Firm* — MASRHALL, GERSTEIN & BORUN LLP

(57)          ABSTRACT

The present invention relates to a method for regulating the operation of a milk pump by applying a vacuum by means of a vacuum source operatively coupled with a control for controlling the operation of the vacuum source and aims to provide such method for pumping milk form the breast of a nursing mother which is able to provide sufficient yield of milk without adversely affecting the breast tissue properties by controlling the operation of the vacuum source such that the control receives a signal indicative of a volume flow (V) of milk and adjusts at least one of the following operational parameters of the vacuum source: vacuum strength, cycle frequency or shape of vacuum profile over time.

17 Claims, 2 Drawing Sheets

(56) References Cited

U.S. PATENT DOCUMENTS

| | | | |
|---|---|---|---|
| 7,641,629 B2 | 1/2010 | Yuen | |
| 2005/0228342 A1* | 10/2005 | Yuen .................. | A61M 1/0697 |
| | | | 604/74 |
| 2016/0206794 A1* | 7/2016 | Makower ............ | A61M 1/0697 |
| 2020/0078503 A1* | 3/2020 | Bartlett ................ | A61M 1/062 |

FOREIGN PATENT DOCUMENTS

| | | | |
|---|---|---|---|
| JP | 2011-507577 A | 3/2011 |
| WO | WO-00/57934 A1 | 10/2000 |
| WO | WO-2003/082378 A1 | 10/2003 |
| WO | WO-2009/081313 A1 | 7/2009 |
| WO | WO-2010/096547 A1 | 8/2010 |

OTHER PUBLICATIONS

Japanese Patent Office (JPO) Application No. 2022-548893 has issued an Office Action, dated Sep. 13, 2023.

* cited by examiner

METHOD FOR REGULATING THE OPERATION OF A MILK PUMP

CROSS-REFERENCE TO RELATED APPLICATION

This present application is the US national phase of International Patent Application No. PCT/EP2021/053592, filed Feb. 15, 2021, which claims priority to European Application No. 20157295.5, filed Feb. 14, 2020. The priority application, EP20157295.5, is hereby incorporated by reference in its entirety.

FIELD OF THE DISCLOSURE

The present invention relates to a method for regulating the operation of a milk pump by applying a vacuum by means of a vacuum source operatively coupled with a control for controlling the operation of the vacuum source.

The present invention in particular relates to such method in a breast pump for drawing breastmilk, in particularly to a motorized, such as and electrically driven breast pump.

BACKGROUND

Breast pumps for use by nursing mothers are well known. They allow nursing women to express the breastmilk as necessary or convenient, and further provide collection of the breastmilk for later use. For some mothers, breast pumps may be a necessity, such as when the child has suckling problems, or if the mother has problems with excessive or deficient milk production, or soreness, deformation or injury of the mammilla.

Manual breast pumps are commonplace, primarily because they are relatively inexpensive and easy to transport. Being manually driven, however, stroke rate and suction pressure produced can be uneven, and operating the pump can ultimately be tiring. Electrically driven breast pumps are also commonplace. They may be of a substantially large size of a non-portable or semi-portable type, typically including a vacuum pump which has an electric motor that plugs into standard house current.

Advantages of this type of pump are ready controllability and regulation of the vacuum, and the ability to pump both breasts at once. That is, the nursing woman has both hands free to hold two breast pump shields in place for pumping of both breasts at the same time. Battery-driven breast pumps have also been developed. These breast pumps have the advantages of controllability and regulation of the vacuum, as well as being easily carried. Such a battery-driven portable breast pump is described in U.S. Pat. No. 4,964,851, for example. This breast pump, sold under the name MINI-ELECTRIC by Medela, Inc., is lightweight and achieves good vacuum (i.e., negative pressure) regulation in preferred limits, for example, between about 30 and about 300 mmHg.

The LACTINA breast pump sold by Medela, Inc. is also another type of breast pump which may be driven by battery as well as house current. It is generally disclosed in U.S. Pat. No. 5,007,899.

Electrically driven motorized breast pumps have almost universally been developed with a single type of "cycle" for a given pump. That is, the driving mechanism for generating the vacuum (negative pressure) to be applied at the breast in the more sophisticated pumps is geared to a particular sequence, or curve, of negative pressure increase (i.e., increasing suction), and then release. This is often aimed at reproducing in some sense the suckling action of an infant, for instance. Breast pumping can cover a range of different conditions, however, such as where the mother's nipples are sore for some reason, there is a state of significant engorgement, some nipple stimulation may be particularly desired, ejection and relaxation may be of particular interest, it may be desired to increase milk production, and so on. To cope with this requirement, WO 2003/082378 A1 discloses a breast pump programmed to generate, among other things, a plurality of differing milk expression sequences, or curves.

WO 2010/096547 A1 disclosed control of an electrically driven motorized breast pump, which mimics a newborn's suction pattern.

Generally, electrically driven motorized breast pumps are controlled to provide at least two different suction patterns. At the beginning of the cycle, fast vacuum cycle frequencies of usually more than 100 cycles per minute are applied to elicit milk ejection, i.e. trigger first milk flow. Apart from this milk let down program, the controller of the breast pump is adapted to apply slower vacuum cycle frequencies resulting in longer vacuum cycles for extracting milk from the breast after once milk ejection, i.e. milk flows occurs. WO 2003/082378 A1 for example discloses a vacuum range of between 100 and 250 mmHg and a frequency of 47 through 78 per minute as operational parameters in the main pump program while the milk let down program or stimulation program applies a vacuum in the range of between 50 and 150 mmHg at cycles of between 120 to 150 per minute. The various programs for controlling the operational parameters of the pumps according to WO 2003/082378 A1 are selected by the user.

The present invention aims to provide a method regulating the operation of a milk pump from the breast of a nursing mother which is able to provide sufficient yield of milk without adversely affecting the breast tissue properties.

As a solution to the above object, the present invention provides a method as defined in claim 1.

This method controls the operation of the vacuum source by adjusting the operation parameters of the vacuum source dependent on the actual volume flow of milk, which volume flow results from the pumping performance of the breast pump.

The breast pump is usually an electrically driven breast pump, which can have the constitution as e.g. described in WO 2003/082378 A1.

The breast pump furthermore has a sensor adapted to sense a volume flow of milk between a breast shield, which is adapted to receive the breast of a nursing mother and usually a collection container in fluid communication with the breast shield. Usually, a milk channel is provided between the breast shield and the collection container, which milk channel is connected to the vacuum source for applying the negative pressure at the mammilla to force the milk flow.

For obtaining a signal indicative of the volume flow of milk, any suitable measurement technique may be used such as counting of droplets of milk on their way from the breast shield to the collection container. For this, the flow of milk can be continuously measured, e.g. as described in US 2015/0283311 A1. It is also feasible to calculate the milk flow from measurements over time of the fluid volume contained in the collection container as e.g. taught in WO 2018/045349 A1. Moreover, a certain volume may be measured in a measuring chamber arranged between the breast shield and the collection container, which measuring chamber has an opening valve and is adapted to store for a certain period the milk to measure the volume collected within the measuring chamber over said time.

All the above measurements, a signal indicative of the volume flow of milk from the breast shield to the collection container may be obtained. The sensor may just measure the existence of volume flow. Thus, the sensor may just provide e.g. a signal indicating the presence or absence of a volume flow.

In other words, the signal indicative of the volume flow of milk may be a signal which continuously provides information on the existence or an amount of the actual volume flow of the milk from the nipple through the breast shield to the collection container. Alternatively, discrete information on the existence or on actual volumes within a chamber and the change over time of said volume may be utilized as a signal indicative of the volume flow of the milk.

On the basis of the signal at least one operational parameter of the vacuum source is adjusted. The operational parameters adjusted in response to the signal indicative of a volume flow of milk may be any operational parameter of the vacuum source, i.e. the pump. However, at least one of the following operational parameters is adjusted in accordance with the information retrieved from the signal indicative of a volume flow of milk: vacuum strength, cycle frequency or shape of vacuum profile over time.

Among those, the vacuum strength is in fact the absolute value of the applied vacuum level. The cycle frequency assumes that a vacuum is applied in a cyclic manner between a maximum vacuum strength, i.e. the highest absolute value for the applied suction, and the lowest suction value, which can be a suction of 0 mmHg.

A suction pressure is usually a negative pressure. For sake of an easy understanding of the technical teaching, the suction pressure applied is referred to as an absolute suction pressure with a high suction pressure providing the highest suction effect at the mammilla and a low suction pressure providing the lowest or no suction effect at the mammilla and/or within any area of the breast pump. The lowest suction pressure usually is 0 mmHg. A suction cycle may also apply some positive pressure on the breast or the nipple.

In addition, the at least one operational parameter to be adjusted in response to the signal indicative of the volume flow may be the shape of the vacuum profile. WO 2003/082378 A1 discloses various vacuum profiles within one specific cycle. The vacuum profile may exhibit a parabolic or sinus curve between the highest value and the lowest suction value. As shown in FIG. 14 of WO 2003/082378 A1, the suction curve may likewise exhibit a specific profile with a peak for the maximum suction force and a plateau next to the peak with a rather steep slope from the lowest suction force, i.e. a suction of 0 mmHg to the plateau or peak. The vacuum profile may result from single or multiple stroke action of a pump as the vacuum source. In response to the signal indicative of the volume flow, the speed of the motor i.e. the pumping aggregate may be altered as well as the speed of the airflow of the air moved within the breast pump.

The operational parameters and the actual profile and value, i.e. strength of the vacuum, cycle frequency or shape of vacuum profile over time, may exist at a specific position of the breast pump, i.e. within the vacuum source, the milk channel, the collection container or the breast shield, in particular close to the mammilla. Due to the compressibility of air, the actual vacuum strength, cycle frequency and/or shape of vacuum profile over time measured e.g. at the mammilla may depart from the operational parameters set in this respect for the pump.

SUMMARY OF THE DISCLOSURE

For carrying out the present invention, it is not decisive where to measure each of the parameters and the constitution of each of the parameters at a specific location within the breast pump. It is, however, decisive to adjust the operational parameters of the vacuum source within the breast pump in response to the actual milk flow during pumping operation of one or more vacuum sources of the devise applying the method.

The present method is in particular applied after commencement of an expression phase, i.e. at or after "let down" the milk. In other words, control and adjustment of the operational parameters in response to the signal indicative of a volume flow of milk is preferably carried out after termination of the stimulation phase and in the so-called expression phase in which milk is collected from the breast.

The operational parameters are continuously or cyclically adapted. In order to avoid unstable operation conditions of the vacuum source in which the vacuum source parameters are instantaneously changed, the control of the vacuum source may apply a holding time for holding the operational parameters set at a certain level and throughout a predetermined period of time once the operational parameters have been set in response to the signal indicative of the volume flow of the milk. Such holding phase may be applied for a few seconds up to minutes. Preferably, the holding time is set between 5 seconds and 300 seconds.

According to a preferred embodiment of the present invention, the signal used to adjust the at least one operational parameter is a signal indicative of a quantitative volume flow of milk. In other words, the actual volume flow and not only the existence or non-existence of milk flow is used for adjusting the at least one operational parameter. The resolution of the volume flow over time may be rather coarse, in particular, if the volume flow is determined periodically by measuring the volume in the measurement chamber. Continuous information on the actual quantity of volume flow may not be required for carrying out the inventive method. It may be sufficient to assign the volume flow to different qualities like e.g. regular volume flow, high volume flow or low volume flow, which low volume flow may include a zero volume flow of milk.

Usually, the operational parameters of the vacuum source, in particular the vacuum strength, the cycle frequency or shape of vacuum profile over time may be selected within a regular range in case the volume flow of milk is between a low flow threshold and a high flow threshold. Such regular or default operational parameters may correspond to those parameters usually applied in the expression phase in the state of the art. Depending on the individual requirements of the user of the breast pump, such default operational conditions may be altered by the user to set parameters which are to optimize volume flow in order to obtain a higher yield under comfortable conditions while they can be adapted to more gentle conditions, if the user feels uncomfortable with the preset default operational parameter or parameter(s).

Once set by the user, the respective operational parameter or parameter(s) are applied as the new regular operational parameters in case the volume flow of milk is between the low flow threshold and the high flow threshold and can be stored as the new default.

Preferably, the default operational parameters will be adjusted to intensify operational parameters of the vacuum source if the signal indicative of the volume flow of milk is above the high flow threshold value. Observations by the inventors have led to the conclusion, that in particular a high volume flow of milk allows the application of intensified operational parameters to the breast of the nursing woman without adversely affecting the comfort level of the user and/or negatively affecting the breast tissue properties. Thus, the preferred embodiment of the inventive method selects intensified operational parameters in case of milk flow above the high flow threshold, which intensified operational parameters are used to obtain a higher yield.

In case of an intensified vacuum strength, respective vacuum strength has a higher absolute value than the regular vacuum strength, which is applied in case the volume flow of milk is between the low flow threshold and the high flow threshold. If for example the default vacuum strength is set at 200 mmHg, the intensified vacuum strength could be a suction force corresponding to 250 mmHg or even 300 mmHg.

The intensified cycle frequency may be lower than the default frequency. In the stimulation phase, the cycle frequency may be set to 100 to 150 cycles per minute while a cycle frequency of about 10 to 78 cycles per minute, preferably about 28 to 78 cycles per minute may be applied in the expression phase and as a volume flow of milk exists. Within said range, the default cycle frequency may be set e.g. between 45 to 99 cycles per minute, preferably between 45 to 78 cycles per minute while the intensified cycle frequency may be between 28 to 44 cycles per minute.

As to the vacuum profile, the regular, i.e. generally applied conditions may apply in case the volume flow of milk is between a low flow threshold and a high flow threshold. An intensified shape of vacuum profile over time may be any such profile which was observed as leading to a higher volume flow i.e. milk expression from the breast. An intensified shape of vacuum profile over time may exhibit a rather steep curve from low or zero vacuum strength values to the maximum suction value with a plateau neighboring the maximum suction value and a steep decline at the end of the cycle returning to low or no vacuum applied at the end of the cycle.

To summarize, the intensified operational parameter or parameters will apply a higher vacuum strength for increasing the efficiency of milk extraction from the breast. A sensor can e.g. notify the volume flow and observe information indicative of the amount of volume flow. A signal of such sensor may be forwarded to an algorithm defined threshold level to alter the operational parameters for shifting to an increased milk output operation. The default operational conditions may per se or after individual adjustment by the user of the breast pump comply with a comfortable operation within the low flow threshold and high flow threshold which operational parameter or parameters will be intensified to increase milk output.

The user's acceptable range for intensified operational parameters like vacuum strength may alter depending on the volume flow, i.e. flow rate of milk from the breast. The sensor can detect a volume flow above the algorithm defined threshold level and can enable the vacuum source system to automatically intensify at least one operational parameter.

According to a preferred embodiment of the present invention, the at least one of the operational parameters of the vacuum source is decreased if the signal indicative of the volume flow of milk is below the low flow threshold. A decreased vacuum strength will be a lower vacuum strength. Such lower vacuum strength can be as low as the vacuum strength applied in the stimulation phase. The decreased vacuum strength may assume a value even below the vacuum strength applied for the stimulation phase. Different vacuum strength values may be applied, which are each lower than the default vacuum strength.

A decreased cycle frequency is a more moderate cycle frequency and may be embodied by applying a larger number of cycles per minute. The decreased cycle frequency may correspond to the frequency applied in the stimulation phase.

A decreased shape of vacuum profile over time may be embodied by a smooth curve of the vacuum as e.g. described as the extremely gentle suction in WO 2003/082378 A1 (compare FIG. 12). Specifically, a smooth transition from a zero suction strength to the maximum suction strength and return to the zero suction strength without sharp edges and sharp increases or decreases in the vacuum strength curve may characterize the decreased shape of vacuum profile over time. Moreover, each cycle may comprise a period of no suction force, which may assume a duration corresponding to 30 to 50% of each cycle time. In other words, a suction force may only be applied over a portion of each vacuum cycle, whereas the remaining portion will not apply any suction force.

Under decreased operational parameters applied, the above mentioned sensor may detect volume flow of milk above the algorithm defined low flow threshold value and can enable the vacuum source to automatically intensify the at least one operational parameter to apply the default parameter and increase milk output after e.g. a period in which in the expression phase no or a very reduced volume flow of milk was detected.

Applying a rather high vacuum strength and slower longer cycles when the flow of milk reduces to low or no flow condition, adversely effects the breast tissue properties encouraging swelling and edema and resulting in constriction of milk ducts and a reduction of milk output. Due to this finding, the present invention preferably proposes to decrease the at least one operational parameters in case of milk flow below the low flow threshold.

In general, the actual amount of milk flowing from the breast shield to the collection container may be utilized as a signal indicative of the volume flow. However, also e.g. the first or the second derivative over time of said signal may be used to compare such value with a preselected threshold value to decide whether one or more of the operational parameters are to be adjusted for coping with different flow conditions or different expected flow conditions.

The first derivative over time approaching a zero value may be utilized to detect a change in the volume flow of milk. If in case of a positive value of the change of volume flow over time, i.e. in case of a positive first derivative over time of the volume flow, the respective first derivative approaches a zero value, a local maximum or an absolute maximum for the volume flow may be reached, which may be a reason to adapt the operational parameters to an intensified or a decreased operational parameter. In case respective first derivative of the volume flow over time, i.e. the change of the volume flow over time is negative and approaches a zero value, an absolute or local minimum of the volume flow of milk curve over time may be approaching, which again may give rise to the need to adapt the at least one operational parameter.

In case of change of the volume flow over time, i.e. the first derivative of the volume over time assuming a high value, the operational parameters may be intensified to increase the efficiency of milk extraction, while the at least one operational parameter may be decreased in case of a low first derivative over time, i.e. a rather slow increase of the volume flow over time, i.e. in a condition the volume flow signal over time reaches a plateau.

A high change of volume over time (dV/dt) is usually between 15 ml/min (0.27 g/s) and 18 ml/min (0.33 g/s) whereas a low dV/dt is between 5 ml/min (0.09 g/s) and 7 ml/min (0.13 g/s).

As mentioned above, the second derivative of the volume flow over time may also be used to adjust the operational parameter by comparing the value of the second derivative of the volume flow over time with preselected threshold values in order to decide adjustment of at least one operational parameter either to intensified or to decreased conditions.

According to an alternative embodiment, which may likewise be implemented in the control of the vacuum source to adapt the at least one operational parameter, the volume flow during at least one vacuum cycle is analyzed to adjust the at least one of the operational parameters of the vacuum source for at least one subsequent vacuum cycle. In other words, not the absolute volume flow obtained in the course of extracting milk from the breast is the decisive basis for setting the operational parameter but the yield of at least one specific previous vacuum cycle to set the at least one operational parameter for a subsequent vacuum cycle, which can be the vacuum cycle directly preceding the previous vacuum cycle. As previously mentioned, a holding time may likewise be applied in this embodiment in order to avoid instantaneous adaption of the operational parameter between each cycle. Accordingly, the at least one vacuum cycle may be plural vacuum cycles and/or the at least one subsequent vacuum cycle may be a sequence of plural vacuum cycles.

According to a preferred embodiment of the present invention, the volume flow of milk during the at least one vacuum cycle is analyzed as to the peak volume flow and/or the total volume flow during the at least one vacuum cycle. Depending on the analysis of said cycle, the at least one operational parameter of the vacuum source is intensified in the at least one subsequent vacuum cycle, if the peak volume flow and/or the total volume flow between an earlier and a later cycle increases. On the other hand, the at least one of the operational parameters of the vacuum source is decreased if the peak flow and/or the total volume flow of a later vacuum cycle is lower than in a vacuum cycle preceding such later vacuum cycle as an earlier vacuum cycle.

The adjustment of the at least one operational parameter on the basis of a cycle-to-cycle analysis may lead to an instantaneous adaption of the operational parameter in response to the actual milk flow conditions, which are evaluated on the basis of peak flow or total volume flow during at least one vacuum cycle.

The preferred embodiment of the method can be carried out by utilizing information indicative of volume flow during the at least one vacuum cycle from a memory. This memory may store data indicative of the volume flow during one specific session, in which the operational parameters are adjusted. Setting of the operational parameters may likewise be carried out on the basis of information obtained by learning from the behavior of the control of the operational parameters in response to a signal indicative of the volume flow of milk. Accordingly, similar control of operational parameters in response to a specific behavior of the volume flow of milk may be taken from the memory to adjust the at least one operational parameter. In other words, the memory may be storing operational parameter history and/or the history of volume flow of milk. As mentioned before, respective data may be obtained during the same session. The memory may likewise store the correlation between at least one operational parameter and the volume flow of milk over time of a previous or all previous sessions and apply those data to the actual control of at least one of the operational parameters during the actual session.

In general, proper setting of the operational parameters according to this preferred embodiment will be carried out on the basis of a history, which history is stored in the memory and which history pertains to the operational parameter history and/or the volume flow of milk history. The operational parameter history may store setting of at least one, preferably all operational parameters of the vacuum source over time. Preferably, those data are stored along with the volume flow of milk history in order to correlate the resulting milk flow of an individual user and correlate the milk ejection efficiency of respective individual user with the setting of the at least one operational parameter.

Thus, the control of the vacuum source is carried out on the basis of experience with the specific user to provide optimum milk extraction efficiency for respective user triggered by a signal indicative of the volume flow of milk.

In summary to the above, the inventive method allows to improve efficiency of milk extraction by applying at least one intensified operational parameter in the event a signal indicative of the volume flow of milk justifies the assumption that the at least intensified operational parameter will increase the volume flow of extracted milk. On the other hand and in case the signal of the volume flow of milk indicates an approaching or existing period of low flow or no flow during the expression of milk, the at least one operational parameter is decreased to avoid a negative influence on the breast tissue properties due to high or regular operational parameters used for generating a higher volume flow than in the no flow or low flow period.

The at least one operational parameters may be set dependent on the actual volume flow of milk. The signal indicative of the volume flow of milk may be analyzed e.g. on the basis of the first derivative over time (dV/dt) or second derivative over time ($d^2V/dt^2$) to identify the transition from an increasing amount of milk flow over time to a decreasing amount of milk flow over time and/or the speed of change of the milk flow to arrive at a different flow rate. As far as the above description refers to the first derivative of the volume flow over time approaching a zero value does not necessarily mean that the actual value of zero for the change of the volume flow over time (dV/dt) must be observed. In fact, a plateau between a first period of increasing milk flow and a second period of increasing milk flow may likewise be considered as a change of the volume flow over time approaching a zero value. The plateau may still show a slight increase in volume flow. The same applies to a plateau between a first decreasing period of the milk flow and a second decreasing period of the milk flow, whereas the plateau may show no change of milk flow or a slight reduction of the milk flow over time.

Alternatively, different vacuum cycles may be compared as to the signal indicative of the milk flow to set the at least one operational parameter for an actual or preceding vacuum cycle. With this control, a single vacuum cycle or multiple vacuum cycles may be analyzed and/or the at least one operational parameter may be set for a single vacuum cycle or multiple subsequent vacuum cycles.

In addition or alternatively, and in particular after a longer period of operation of the breast pump, control of the vacuum source in response to the signal indicative of the milk flow may be adjusted on the basis of a history, specifically on the basis of a correlation between setting or adjusting of the at least one operational parameter and the response of the specific user with respect to milk extraction rate, i.e. volume flow of milk. This aspect is in particular suitable to cope with individual demands and behavior of a specific user. The system preferably employs artificial intelligence to improve operational parameter setting with respect to volume flow of milk to finally be able to set the at least one operational parameter which is best suited for the individual user in order to optimize milk flow on the one hand and gently treat the breast tissue in periods of no flow.

The present invention likewise relates to a beast pump having a control adopted to control the vacuum source as explained above.

The present invention will now be further explained by referring to different embodiments of the invention and referring to the Figures. In the Figures:

BRIEF DESCRIPTION OF THE SEVERAL VIEWS OF THE DRAWING

FIGS. 2a and 2b combined in their aligned arrangement provide, as FIG. 2, an example for a cycle-to-cycle analysis with graphs correlating the volume flow of milk over time (FIG. 2b) to and the vacuum strength applied in each cycle (FIG. 2a).

DETAILED OF THE PREFERRED EMBODIMENTS

Figures 1A, 1B, 1C, 1D, 1E:
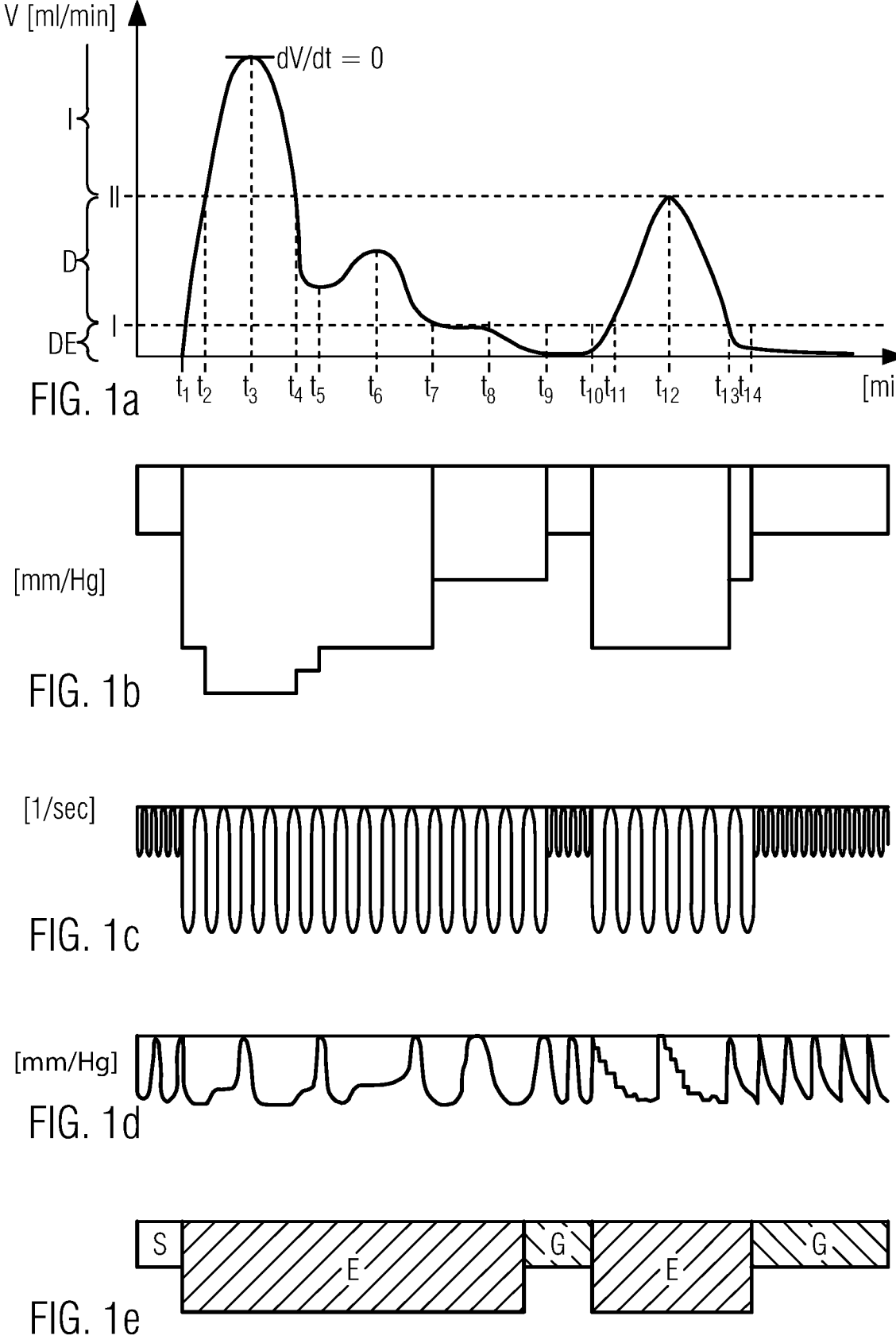
FIG. 1a is a plot correlating the volume flow of milk over time.
FIG. 1b is a plot of the vacuum strength over time.
FIG. 1c is a plot of the cycle frequency over time.
FIG. 1d is a plot of the vacuum profile over time.
FIG. 1e is a plot illustrating different phases during the stimulation and expression phase, with FIGS. 1a thru 1e intended to be viewed collectively in their aligned arrangement as FIG. 1.

In FIG. 1a, the ordinate identifies the actual value of the volume flow whereas the abscissa relates to the time. At time t=0, the stimulation phase is applied. As a reaction thereof, let down of milk will eventually take place at t1. t1 identifies the first noticeable volume flow of milk. Shortly after t1, the volume curve will intersect with a low flow threshold line I, which corresponds to a volume flow of milk of 5 ml/min (0.09 g/s). At t2, the volume flow curve will intersect with a high flow threshold line II at 11.9 ml/min (0.22 g/s). Between t2 and t4, the volume flow of milk is above this high flow threshold value II. As a consequence, intensified operational parameters are applied, which will be further explained by referring to FIGS. 1b through 1d.

In the stimulation phase and prior to t1, a stimulation vacuum strength of about 50 mmHg (FIG. 1b) and a cycle frequency of between 100 and 120 cycles per minute (FIG. 1c) will be applied. The curve shape (FIG. 1d), i.e. the vacuum profile over time has a parabolic form with the maximum in the middle of each cycle but a smooth transition from the 0 mmHg value to the maximum vacuum strength. In FIG. 1d, the curves all reach to 100% vacuum strength, wherein the vacuum strength level for each of the curves may be different and can be retrieved from FIG. 1b.

Sensing a first volume flow of milk at t1, the operational parameters of the stimulation phase are shut off by the control of the breast pump and the operational parameters for the expression phase control the performance of the vacuum source of the breast pump. With the commencement of milk flow, the regular, i.e. default operational parameters are used to control the vacuum source. The cycle frequency is set lower than in the stimulation phase. The regular cycle frequency is set at 50 CPM. The vacuum profile exhibits a sharp increase of the vacuum in each cycle for reaching a plateau at the maximum vacuum strength, which plateau will decline to a further plateau of about 80% of the maximum vacuum strength. At the end of the plateau, the vacuum will fall to 0 mmHg to shortly thereafter rise to reach the next plateau for the next vacuum profile. Respective vacuum profile over time will be applied with each cycle frequency. This is not properly reflected in FIGS. 1c and 1d due to the need to elucidate some details of the vacuum profile over time in the drawing.

The cycle frequency and the cycle profile, however, do not have to directly result from the stroke action of a vacuum pump forming the vacuum source on a general basis. Each cycle frequency and/or each vacuum profile over time can result from multiple strokes of the pump, which pump may have additional chambers to store and/or valves to control the actual vacuum, the profile of the vacuum over time and possibly the vacuum frequency, e.g. at the breast shield or in the milk channel.

As evident from the comparison of FIGS. 1a and 1c and 1d, the default operational parameters for the cycle frequency and the vacuum profile over time are the same irrespective of the actual volume flow of milk being below or above the high flow threshold II. However, and as evident at t4, the vacuum strength will be lowered in case the volume flow intersects with the high flow threshold with a negative $dV/dt$, i.e. a decline phase of the volume curve. At t5, a value $dV/dt=0$ is observed, which triggers the setting of the regular vacuum strength.

Between t2 and t4, the intensified operational parameters for the cycle frequency and the vacuum profile over time as well as the vacuum strength are applied. As evident, the intensified vacuum strength is higher than the regular vacuum strength before t1. On the other hand, the intensified cycle frequency and the intensified vacuum profile over time are the same as the respective default operational parameters between t1 and t2.

At t6, a $dV/dt$ is observed between $dV/dt>0$ and $dV/dt<0$. This observation, however, lies between the high flow threshold II and the low flow threshold I, and thus will not lead to an adjustment of the operational parameters of the vacuum source in the exemplified embodiment.

At t7, the flow curve intersects with the low flow threshold I. As a consequence, the vacuum strength is lowered to 80 mmHg, which is a first decreased vacuum strength. The cycle frequency will be raised to 78 CPM, which is a first decreased cycle frequency value, whereas a first decreased curve shape is exemplified in FIG. 1d corresponds to the curve of the stimulation phase.

Between t9 and t10, the flow volume is very low and finally zero. Thus, the vacuum strength is further reduced to a second decreased level of 50 mmHg, while a cycle frequency of 100 to 120 cycles per minute is applied as in the stimulation phase, which represents a second decreased cycle frequency. The curve shape between t9 and t10 is essentially the same as between t7 and t9. This decreased shape of vacuum profile over time shows a smooth increase and decrease with no plateau. It corresponds to a sinus curve with an absolute minimum value corresponding to a 0 mmHg vacuum strength.

While the volume flow profile between t10 and t11, i.e. the profile from zero flow to a flow value above the low flow threshold at t11 may be similar to the volume flow curve after t1, the control of the pump is aware of the fact that this volume flow behavior is observed in the expression phase. While the vacuum strength and the cycle frequency are set "default" as before, the vacuum profile over time between t11 and t13, i.e. between the high flow threshold II and the low flow threshold I shows a different curve than between t1 and t7. The vacuum profile over time shows multiple steps from zero to the maximum strength value and a steep decline from there to the zero line before the next cycle begins.

After t13, the volume flow of milk is further reduced and finally dries up at t14. In this period, a decreased shape of the vacuum profile is applied with a rather sharp edge between rise of the vacuum and fall of the vacuum to the zero line. The cycle frequency between t13 and t14 is the same as between t10 and t13. The vacuum strength is as between t7 and t9, i.e. 80 mmHg.

After t14, a decreased vacuum strength of 50 mmHg as in the stimulation phase is applied. The cycle frequency is the same as in the stimulation phase. The vacuum profile over time after t14 exhibiting a decreased vacuum profile is the same as between t13 and t14.

As evident from FIG. 1e, in the expression phase and after simulation, i.e. after t1, extraction of milk from the user's breast is at issue. Between t8 and t10, control of the vacuum source to gently treat the breast tissue is the ultimate goal for control of the vacuum source. The regime trying to optimize milk extraction is intensified with E in FIG. 1e, whereas the general treatment of the tissue is identified with G.

As the milk flow rises after t10, the gentle regime G is shifted to the extraction regime E to improve efficiency of milk extraction, whereas intersecting the low flow threshold I with a negative dv/dt, i.e. as the milk flow is declining will place the gentle treatment regime G into effect (compare FIG. 1e).

The above description of FIG. 1 is just an example. Adjustment of the operational parameters in this embodiment is mostly triggered by the threshold I, II. It could, however, be triggered by the first derivative over time. If, for example, the increase in volume flow between t1 and t2 is considered to be high, observation of such change of volume flow over time dV/dt may likewise trigger adjustment of the operational parameters. On the other hand, if the decline between t4 and t5 is considered to be high, and as the volume curve has a negative dV/dt, a very high absolute value of dV/dt may likewise trigger transition from intensified operational parameters to default or decreased.

Figures 2A, 2B:
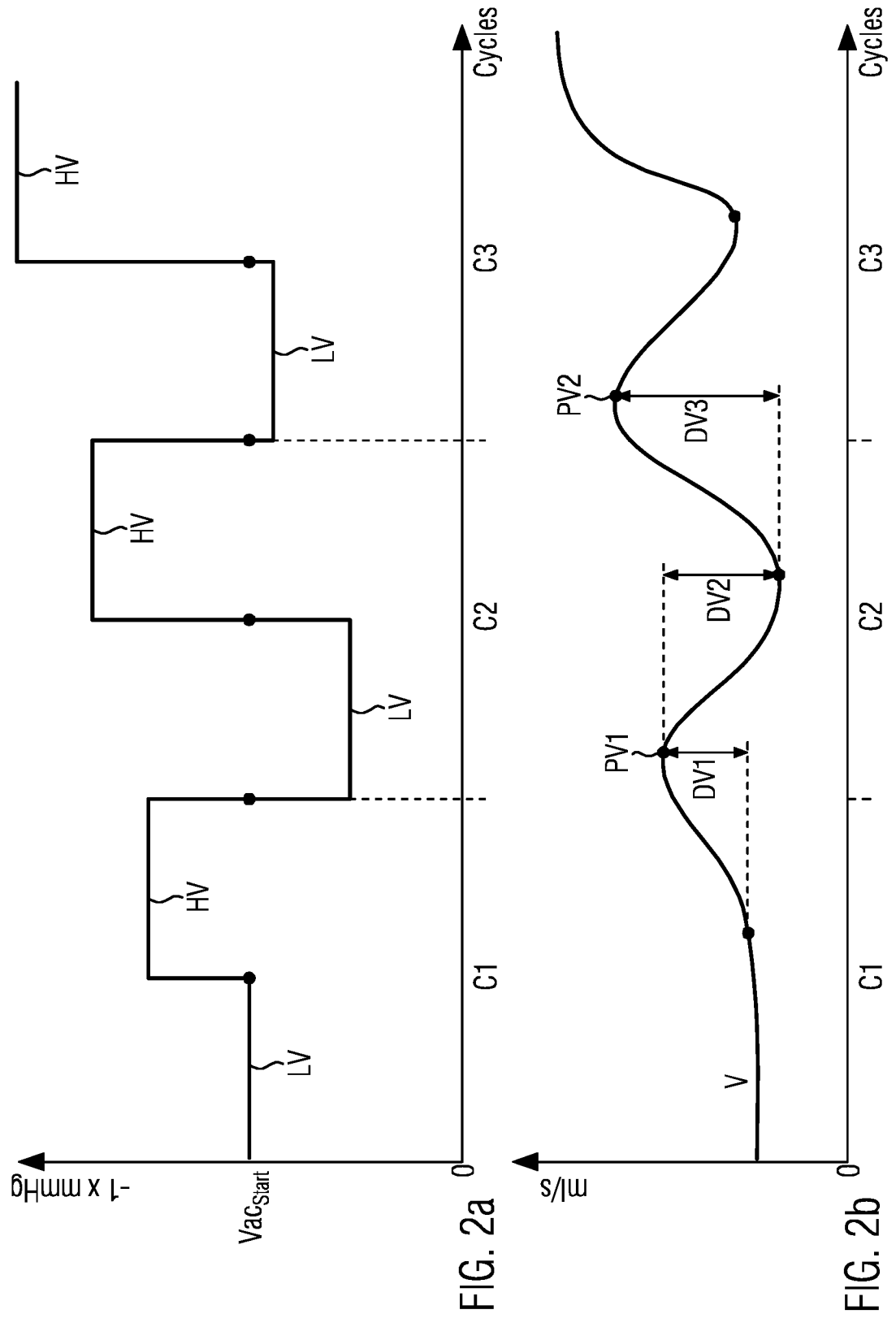
FIG. 2a is a graph of vacuum strength applied in each cycle.
FIG. 2b is a graph of the volume flow of milk over time.

FIG. 2 exemplifies an adjustment of the vacuum strength as the only operational parameter on a cycle-to-cycle basis. In said embodiment volume flow as observed in FIG. 2b is analyzed as a response to an applied cycle C1; C2; C3 (FIG. 2a). Note that the ordinate of FIG. 2a has negative pressure values on the positive scale.

DV1, DV2 and DV3 are each subsequent peak flow differences. DV2 for example is the difference between peak flow PV1 due to a first cycle C1 and a minimum flow observed in the second cycle C2. Each cycle C1, C2, C3 has a high phase vacuum strength HV and a low phase vacuum strength LV. In each subsequent cycle DV-values increase over time and thus cycle. Thus, a positive development of volume flow over time is observed.

Due to this, the high phase vacuum strength HV for the second cycle C2 is set higher than in C1, whereas the low phase vacuum strength LV in said second cycle C2 is set lower than in C1. Thus, the absolute pressure difference on the mammilla will be raised in subsequent cycles C1, C2. As the respective finding results from comparing DV3 with DV2 the absolute pressure difference between LV and HV and/or the vacuum strength HV at the high phase of a cycle C may be raised and thus intensified in expectation of a further increase of volume flow in a later cycle C4 or C5 or C6 (not shown).

The absolute volume flow PV2 in cycle C2 is also higher in comparison to the peak volume flow PV1 in the earlier cycle C1, which may constitute another criterion to intensify the vacuum strength in the next cycle C3.

The invention claimed is:

1. A method for regulating the operation of a milk pump by applying a vacuum by means of a vacuum source operatively coupled with a control for controlling the operation of the vacuum source, wherein the control receives a signal indicative of a volume flow (V) of milk and adjusts at least one of the following operational parameters of the vacuum source: vacuum strength, cycle frequency or shape of vacuum profile over time, and wherein the at least one of the operational parameters of the vacuum source is intensified if a positive value of a change of the volume flow (V) over time (dV/dt) approaches a zero value.

2. The method of claim 1, wherein the at least one of the operational parameters is adjusted after commencement of an expression phase (E, G).

3. The method of claim 1, wherein the signal is indicative of a quantitative volume flow (V).

4. The method of claim 1, wherein at least one of the operational parameters of the vacuum source is set on default (D) if the signal indicative of the volume flow (V) of milk is between a low flow threshold and a high flow threshold.

5. The method of claim 4, wherein the at least one of the operational parameters of the vacuum source is intensified (1), if the signal indicative of the volume flow (V) of milk is above the high flow threshold.

6. The method of claim 4, wherein the at least one of the operational parameters of the vacuum source is decreased (DE), if the signal indicative of the volume flow (V) of milk is below the low flow threshold.

7. The method of claim 6, wherein the at least one of the operational parameters of the vacuum source applied during stimulation(S) is selected in an expression phase (E, G), if the signal indicative of the volume flow (V) of milk is below the low flow threshold.

8. The method of claim 4, wherein all of the operational parameters are set on default (D) if the signal indicative of a volume flow (V) of milk is between the low flow threshold and the high flow threshold.

9. The method of claim 1, wherein the value of the change of the volume flow (V) over time (dV/dt) is analyzed and that the at least one of the operational parameters of the vacuum source is intensified in case of a high value of the change of the volume flow (V) over time (dV/dt) and is decreased in case of a low value of the change of the volume flow (V) over time (dV/dt).

10. The method of claim 1, wherein the volume flow (V) during at least one vacuum cycle (C1, C2, C3) is analyzed to adjust the at least one of the operational parameters of the vacuum source for at least one subsequent vacuum cycle (C2, C3).

11. The method according of claim 10, wherein information indicative of volume flow (V) during the at least one vacuum cycle is obtained from a memory storing operational parameter history and/or volume flow (V) of milk history.

12. The method of claim 1, wherein the volume flow (V) during at least one vacuum cycle (C1, C2, C3) is analyzed as to a peak volume flow (V) and/or a total volume flow (V) during said at least one vacuum cycle (C1, C2, C3), wherein at least one of the operational parameters of the vacuum source is intensified in at least one subsequent vacuum cycle (C2, C3) if the peak volume flow (PV1, PV2) and/or the total volume flow (V) increases between an earlier and a later vacuum cycle, and wherein at least one of the operational parameters of the vacuum source is decreased in at least one subsequent vacuum cycle (C2, C3) if the peak volume flow (V) and/or the total volume flow (V) decreases between an earlier and a later vacuum cycle.

13. The method of claim 1, wherein the at least one of operational parameters is adjusted on the basis of data stored in a memory storing operational parameter history and/or volume flow (V) of milk history.

14. A method for regulating the operation of a milk pump by applying a vacuum by means of a vacuum source operatively coupled with a control for controlling the operation of the vacuum source, wherein the control receives a signal indicative of a volume flow (V) of milk and adjusts at least one of the following operational parameters of the vacuum source: vacuum strength, cycle frequency or shape of vacuum profile over time, wherein at least one of the operational parameters of the vacuum source is set on default (D) when the signal indicative of a volume flow (V) of milk is between a low flow threshold and a high flow threshold, wherein the at least one of the operational parameters of the vacuum source is intensified (I), when the signal indicative of the volume flow (V) of milk is above the high flow threshold, and and wherein the at least one of the operational parameters of the vacuum source is decreased (DE), when the signal indicative of the volume flow (V) of milk is below the low flow threshold.

15. A method for regulating the operation of a milk pump by applying a vacuum by means of a vacuum source operatively coupled with a control for controlling the operation of the vacuum source, wherein the control receives a signal indicative of a volume flow (V) of milk and adjusts at least one of the following operational parameters of the vacuum source: vacuum strength, cycle frequency or shape of vacuum profile over time, wherein a value of a change of the volume flow (V) over time (dV/dt) is analyzed and that the at least one of the operational parameters of the vacuum source is intensified in case of a high value of the change of the volume flow (V) over time (dV/dt) and is decreased in case of a low value of the change of the volume flow (V) over time (dV/dt), wherein the volume flow (V) during at least one vacuum cycle (C1, C2, C3) is analyzed as to a peak volume flow (V) and/or a total volume flow (V) during said at least one vacuum cycle (C1, C2, C3);

wherein the at least one of the operational parameters of the vacuum source is intensified in at least one subsequent vacuum cycle (C2, C3) when the peak volume flow (PV1, PV2) and/or the total volume flow (V) increases between an earlier and a later vacuum cycle, and wherein at least one of the operational parameters of the vacuum source is decreased in at least one subsequent vacuum cycle (C2, C3) when the peak volume flow (V)

and/or the total volume flow (V) decreases between an earlier and a later vacuum cycle.

16. A milk pump, comprising:

a vacuum source; and a control operatively coupled with the vacuum source for controlling the operation of the vacuum source to apply a vacuum;

wherein the control is configured to:

receive a signal indicative of a volume flow (V) of milk and adjust at least one operational parameter of the vacuum source based on the signal indicative of the volume flow (V) of milk, the at least one operational parameter comprising at least one of: vacuum strength, cycle frequency, or shape of vacuum profile over time;

set the at least one operational parameter of the vacuum source to default (D) when the signal indicative of the volume flow (V) of milk is between a low flow threshold and a high flow threshold;

set the at least one operational parameter of the vacuum source to intensified (I), when the signal indicative of the volume flow (V) of milk is above the high flow threshold; and set the at least one operational parameter of the vacuum source to decreased (DE), when the signal indicative of the volume flow (V) of milk is below the low flow threshold.

17. A milk pump, comprising:

a vacuum source; and a control operatively coupled with the vacuum source for controlling the operation of the vacuum source to apply a vacuum;

wherein the control is configured to:

receive a signal indicative of a volume flow (V) of milk and adjust at least one operational parameter of the vacuum source based on the signal indicative of the volume flow (V) of milk, the at least one operational parameter comprising at least one of: vacuum strength, cycle frequency, or shape of vacuum profile over time;

analyze a value of a change of the volume flow (V) over time (dV/dt);

intensify the at least one operational parameter of the vacuum source in case of a high value of the change of the volume flow (V) over time (dV/dt) and decrease the at least one operational parameter of the vacuum source in case of a low value of the change of the volume flow (V) over time (dV/dt);

analyze the volume flow (V) during at least one vacuum cycle (C1, C2, C3) as to a peak volume flow (V) and/or a total volume flow (V) during said at least one vacuum cycle (C1, C2, C3);

intensify the at least one operational parameter of the vacuum source in at least one subsequent vacuum cycle (C2, C3) when the peak volume flow (PV1, PV2) and/or the total volume flow (V) increases between an earlier and a later vacuum cycle; and decrease the at least one operational parameter of the vacuum source in at least one subsequent vacuum cycle (C2, C3) when the peak volume flow (V) and/or the total volume flow (V) decreases between an earlier and a later vacuum cycle.

* * * * *